(12) United States Patent
Prevost

(10) Patent No.: US 10,736,667 B2
(45) Date of Patent: Aug. 11, 2020

(54) SPINAL IMPLANT SYSTEM AND METHODS OF USE

(71) Applicant: Warsaw Orthopedic, Inc, Warsaw, IN (US)

(72) Inventor: Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 3 days.

(21) Appl. No.: 15/727,311

(22) Filed: Oct. 6, 2017

(65) Prior Publication Data
US 2019/0105080 A1    Apr. 11, 2019

(51) Int. Cl.
*A61B 17/70* (2006.01)

(52) U.S. Cl.
CPC ...... *A61B 17/7032* (2013.01); *A61B 17/7035* (2013.01); *A61B 17/7038* (2013.01); *A61B 17/7076* (2013.01); *A61B 17/7077* (2013.01); *A61B 17/708* (2013.01)

(58) Field of Classification Search
CPC ........ A61B 17/70–7046; A61B 17/7074–7092
See application file for complete search history.

(56) References Cited

U.S. PATENT DOCUMENTS

| | | | | |
|---|---|---|---|---|
| 7,491,208 B2* | 2/2009 | Pond, Jr. | ............ | A61B 17/7082 606/104 |
| 7,988,698 B2* | 8/2011 | Rosenberg | ......... | A61B 17/7086 606/265 |
| 8,444,681 B2* | 5/2013 | Jackson | ............ | A61B 17/7032 606/300 |
| 8,709,015 B2* | 4/2014 | Kolb | .................. | A61B 17/7032 606/246 |
| 9,956,003 B2* | 5/2018 | Prevost | .............. | A61B 17/7035 |
| 2002/0095153 A1* | 7/2002 | Jones | ................. | A61B 17/7037 606/86 A |
| 2006/0009775 A1* | 1/2006 | Dec | ..................... | A61B 17/7088 606/86 R |
| 2007/0161998 A1* | 7/2007 | Whipple | ............ | A61B 17/7032 606/86 A |
| 2007/0255284 A1* | 11/2007 | Miller | ................ | A61B 17/7032 606/252 |
| 2008/0009863 A1* | 1/2008 | Bond | ................... | A61B 17/025 606/86 A |
| 2009/0222046 A1* | 9/2009 | Gorek | .................... | A61B 17/02 606/279 |
| 2010/0179602 A1* | 7/2010 | Dauster | ............. | A61B 17/7032 606/308 |
| 2010/0331849 A1* | 12/2010 | Riesinger | ........... | A61B 17/7077 606/90 |
| 2011/0098755 A1* | 4/2011 | Jackson | ............. | A61B 17/7008 606/305 |
| 2015/0282844 A1* | 10/2015 | Vedula | ............... | A61B 17/7032 606/305 |

* cited by examiner

*Primary Examiner* — Nicholas J Plionis
*Assistant Examiner* — Steven J Cotroneo
(74) *Attorney, Agent, or Firm* — Sorell, Lenna & Schmidt, LLP

(57) ABSTRACT

An instrument includes a shaft and a mating element that extends from the shaft. The mating element is configured to engage a mating element of a bone fastener to move a receiver of the bone fastener relative to a bone anchor of the bone fastener. Implants, systems, constructs, instruments and methods are disclosed.

20 Claims, 11 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including a bone fastener.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, an instrument is provided. The instrument comprises a shaft and a mating element that extends from the shaft. The mating element is configured to engage a mating element of a bone fastener to move a receiver of the bone fastener relative to a bone anchor of the bone fastener. In some embodiments, systems, implants, constructs, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
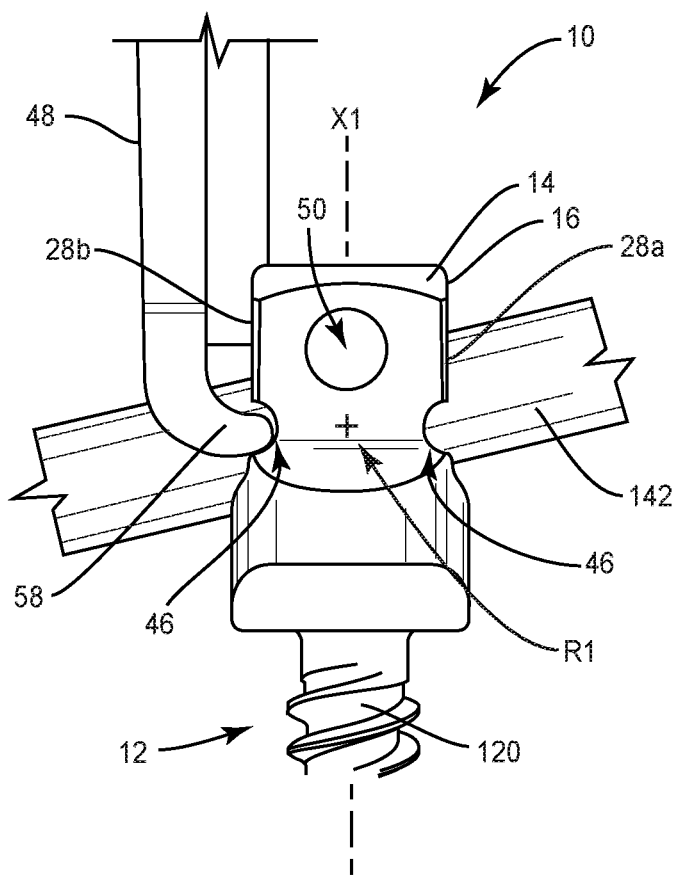
FIG. 1 is a break away, side view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In one embodiment, the spinal implant system includes a bone fastener having a head portion, such as, for example, a receiver that is movable relative to an anchor portion, such as, for example, a bone anchor using a tool engageable with the receiver. In some embodiments, the bone fastener is employed with a method for manipulating a spine.

In some embodiments, the spinal implant system is configured for use with a longitude trauma system with fixed angular screws and/or sagittal angular screws to provide a minimally invasive surgical approach to treat burst fractures by allowing controlled distraction and controlled lordosis correction. In longitude trauma systems, one extender is coupled to each of a plurality of bone fasteners, such as, for example, the bone fasteners included in the spinal implant system. Two racks are included, wherein one of the racks is positioned at midpoints or bottom portions of the extenders and the other rack is positioned at top portions of the extenders to distract ranges of distance between the extenders. This configuration allows a medical practitioner to compress the rack positioned at the top portions of the extenders, while keeping distraction using the rack positioned at the midpoints or bottom portions of the extenders. Rotation of the extenders with respect the bottom rack allows lordosis to be restored.

In some embodiments, the spinal implant system provides lower cost components with transverse angulation capability. In some embodiments, the spinal implant system provides for sagittal correction at the rod. In some embodiments, the spinal implant system includes a decoupled mechanism to control distraction and lordosis at the burst fracture level. In some embodiments, the spinal implant system is capable of being used in a minimally invasive surgical approach or an open surgical approach.

In some embodiments, the bone fastener can be utilized as a multi-axial or uni-axial screw. In some embodiments, the bone fastener is configured for adjusting the orientation of the receiver relative to the bone anchor using a tool engageable with the receiver. In some embodiments, the adjustment of the bone fastener facilitates use in burst fracture reduction and/or deformity correction procedures. In some embodiments, the bone anchor can be locked at various angles relative to the receiver after the tool moves the receiver to dispose the receiver at a desired orientation relative to the bone anchor. In some embodiments, the tool rotates the receiver laterally. In some embodiments, the tool rotates the receiver laterally at a center of rotation of a rod that is disposed within an implant cavity of the receiver. In some embodiments, the receiver includes lateral slots configured for disposal of the tool. In some embodiments, the receiver includes lateral slots configured for disposal of the tool and vertical slots configured for disposal of another instrument. In some embodiments, the lateral slots are spaced apart from the vertical slots. In some embodiments, the lateral slots merge with the vertical slots such that the lateral slots are in communication with the vertical slots. In some embodiments, the lateral slots are defined by a non-linear surface. In some embodiments, the lateral slots are V-shaped cuts. In some embodiments, the lateral slots extend all the way through the receiver. In some embodiments, the lateral slots extend only partially into the receiver without extending all the way through the receiver. In some embodiments, the tool has a tip configured for disposal in the lateral slots. In some embodiments, the tip of the tool has a ball nose. In some embodiments, the tool is configured to rotate relative to the receiver when the tip of the tool is disposed in at least one of the lateral slots. This configuration allows rotation of the receiver with respect to a spinal rod disposed within the implant cavity of the receiver from the tip of the tool.

In some embodiments, the tool rotates the receiver in the transverse plane to properly fit a spinal rod within the implant cavity of the receiver, while stilling allowing rotation of the receiver for sagittal correction. This configuration allows the rod to be properly positioned within a plurality of bone fasteners wherein the position of the receivers of the bone fasteners is off slightly, such as, for example, by one or two millimeters. That is, allowing the receiver to rotate relative to the bone anchor allows proper alignment of the rod with respect to the bone fasteners, without having to bend the rod.

In some embodiments, the bone fastener includes a crown and a retaining ring or snap ring. The crown is positioned on top of a head of the bone anchor and the snap ring is positioned about the head of the bone anchor. The receiver includes an inner surface defining a recess configured for disposal of the snap ring to couple the bone anchor and the crown with the receiver. In some embodiments, the crown has a tapered tip configured to engage a top surface of the head of the bone anchor to force rotation of the bone anchor relative to the receiver. In some embodiments, the spinal implant system is configured to selectively lock a spinal rod and the bone fastener in an angular orientation. In some embodiments, the spinal implant system is configured to selectively lock a spinal rod and the bone fastener in an angular orientation in a single step. In some embodiments, the bone anchor is configured to lock at an angle relative to the receiver. In some embodiments, the bone anchor is configured to lock at an angle relative to the spinal rod. In some embodiments, the bone fastener includes a setscrew that provides an axial force upon the spinal rod, which causes the spinal rod to bear down on the crown such that the crown applies a force upon the head of the bone anchor to fix the bone anchor relative to the receiver. In some embodiments, the axial force is applied along a longitudinal axis defined by the bone anchor. In some embodiments, the crown is made of titanium. In some embodiments, the crown is made of cobalt chrome.

In some embodiments, the head of the bone anchor includes two flats on an outer surface of the head that will key the receiver to control transverse angulation in the coronal plane. That is, the flats on the head of the bone anchor engage flats in the receiver to allow the bone anchor to rotate relative to the receiver in only one plane. It is envisioned that the flats of the bone anchor and the receiver may be oriented to control angulation in other planes, such as, for example, the sagittal plane or the coronal plane, as discussed herein. In some embodiments, the flats are opposite one another such that the flats extend parallel to one another.

In some embodiments, the crown has a small thru-hole for a guidewire. In some embodiments, the thru-hole in the crown has a maximum diameter that is less than that of a tool socket in the head of the bone anchor. This configuration allows the crown to have increased surface area that allows the crown to lock relative to the receiver while providing for sagittal angulation. In some embodiments, the crown engages the head of a bone anchor after the bone anchor is inserted into a pedicle or other portion of a patient's anatomy. In some embodiments, the crown is rotatable about the head of a bone anchor. In some embodiments, the crown is also rotatable relative to the receiver of the bone fastener. In some embodiments, the crown does not include a thru-hole or any other aperture that extends through opposite top and bottom surfaces of the crown. In some embodiments, the receiver has an implant cavity that is boxier than receivers having a U-shaped implant cavity, to allow for greater angulation.

In some embodiments, the spinal implant system is employed with a method for treating a spine, which includes moving the receiver relative to the bone anchor using a tool that is engageable with the receiver to dispose a spinal rod disposed within an implant cavity of the receiver at a desired orientation relative to the bone anchor. In some embodiments, the tool is a distractor, such as, for example, a parallel distractor that can be attached to an extender for controlled sagittal correction. In some embodiments, the spinal implant system has transverse capability that allows for proper alignment between two screws to eliminate the need for a complex parallel distractor. In some embodiments, the method includes the step of decreasing the final screw angle such that the bone anchor is fully aligned with the receiver.

In some embodiments, the spinal implant system is configured for tumor treatment. In some embodiments, the spinal implant system is configured for lordosis correction while still having at least some articulation in the uniplane for at least some coronal adjustment, wherein a spinal rod is at least partially offset. In some embodiments, the spinal implant system includes bone fasteners that combine the benefits of screws that allow for adjustment in the sagittal plane and screws that allow for adjustment in the coronal plane, while still providing at least some angulation.

In some embodiments, the crown is rotatable relative to the head of the bone anchor in the sagittal plane. In some embodiments, the head of the bone anchor is spherical. In some embodiments, the spinal implant system includes a spinal rod that is locked in place with the receiver using a retaining mechanism, such as, for example, a set screw. In some embodiments, the set screw applies a force upon the rod such that the rod, the crown and the spherical head of the bone anchor to allow the rod to be locked relative to the bone anchor and the receiver, while maintaining the orientation of the rod.

In some embodiments, the receiver, the crown and the snap ring form an assembly that may be snapped on or popped on the bone anchor. This configuration allows the bone anchor to be implanted before the receiver, the crown and the snap ring are attached with the bone anchor. In embodiments wherein the crown includes a thru-hole and the bone anchor is cannulated and includes two flats on the outside surface, a guide wire may be inserted through the bone anchor, crown, snap ring and receiver such that the bone anchor, crown, snap ring and receiver may move to the bone anchor, crown, snap ring and receiver to a desired location, such as, for example, a vertebra. A tool, such as, for example, pliers may then be used to engage the flats of the bone anchor to rotate the bone anchor and fix the bone anchor with the vertebra. The crown, snap ring and receiver may then be coupled to the bone anchor.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-13, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

In some embodiments, spinal implant system 10 comprises a bone fastener, such as, for example, a bone screw 12 that includes a member, such as, for example, a receiver 14 connected with a member, such as, for example, a bone anchor 120. Receiver 14 extends along and defines an axis X1, as shown in FIG. 1. Receiver 14 includes a pair of spaced apart arms 16, 18 that define an implant cavity 20 therebetween configured for disposal of a component of a spinal construct, such as, for example, a spinal rod 142.

Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone screw 12. In some embodiments, arms 16, 18 are connected at proximal and distal ends thereof such that receiver 14 defines a closed spinal rod slot.

Figure 2:
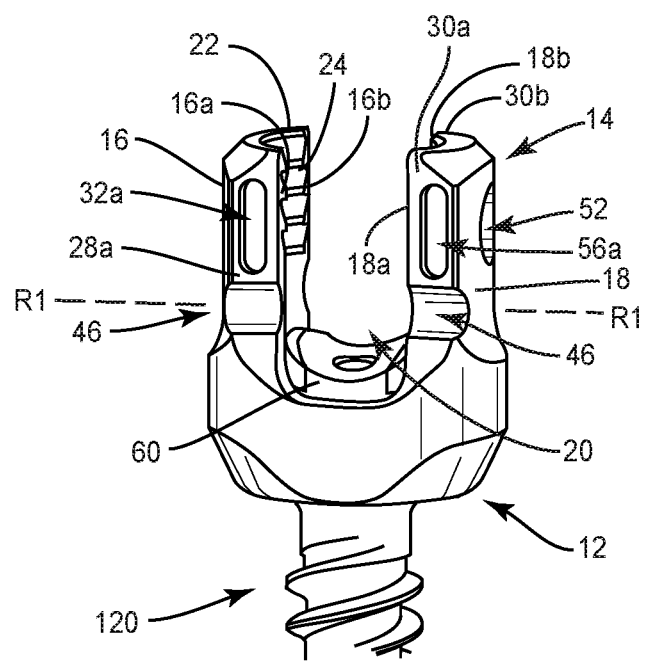
FIG. 2 is a break away, side view of components of the spinal implant system shown in FIG. 1.
Figure 5:
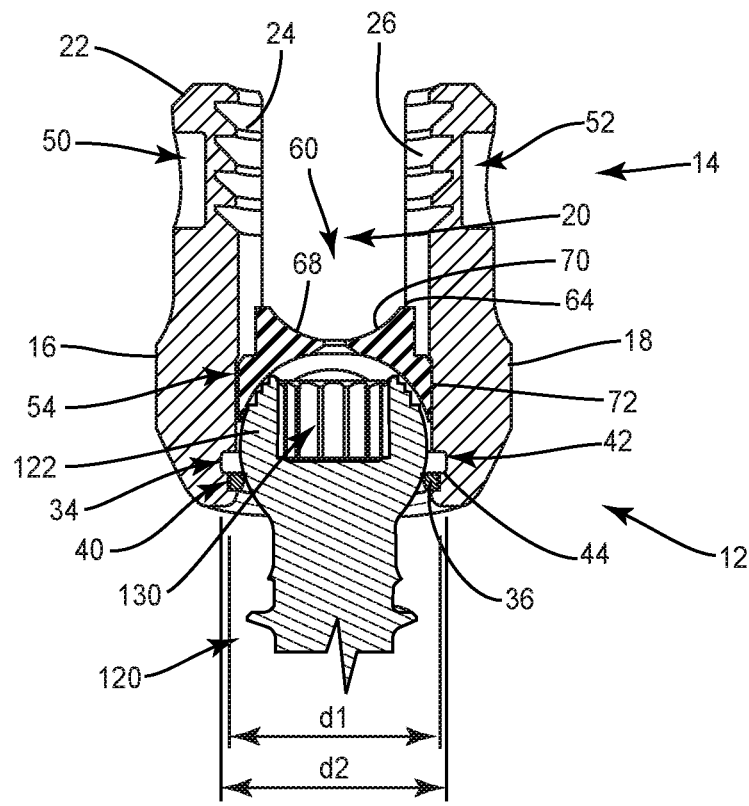
FIG. 5 is a break away, side, cross sectional view of components of the spinal implant system shown in FIG. 1.

Cavity 20 is substantially U-shaped. In some embodiments, cavity 20 is less rounded or boxier to allow more angulation for rod 142 when rod 142 is disposed within cavity 20. That is, the portions of receiver 14 between arms 16, 18 are planar or less rounded than in embodiments in which cavity 20 is U-shaped. In some embodiments, all or only a portion of cavity 20 may have alternate cross section configurations, such as, for example, closed, V-shaped, W-shaped, oval, oblong, triangular, square, polygonal, irregular, uniform, non-uniform, offset, staggered, and/or tapered. Receiver 14 includes a surface, such as, for example, a wall 22. A portion of wall 22 includes a thread form 24 located adjacent arm 16, as shown in FIG. 2, and a thread form 26 located adjacent arm 18, as shown in FIG. 5. Thread forms 24, 26 are each configured for engagement with a coupling member, such as, for example, a setscrew 140, to retain a spinal construct, such as, for example, a spinal rod 142 within cavity 20, as shown in FIG. 5 for example. In some embodiments, wall 22 may be disposed with the coupling member in alternate fixation configurations, such as, for example, friction fit, pressure fit, locking protrusion/recess, locking keyway and/or adhesive. In some embodiments, all or only a portion of wall 22 may have alternate surface configurations to enhance engagement with a spinal rod and/or a setscrew, such as, for example, rough, arcuate, undulating, mesh, porous, semi-porous, dimpled and/or textured. In some embodiments, receiver 14 may include alternate configurations, such as, for example, closed, open and/or side access.

Figure 6:
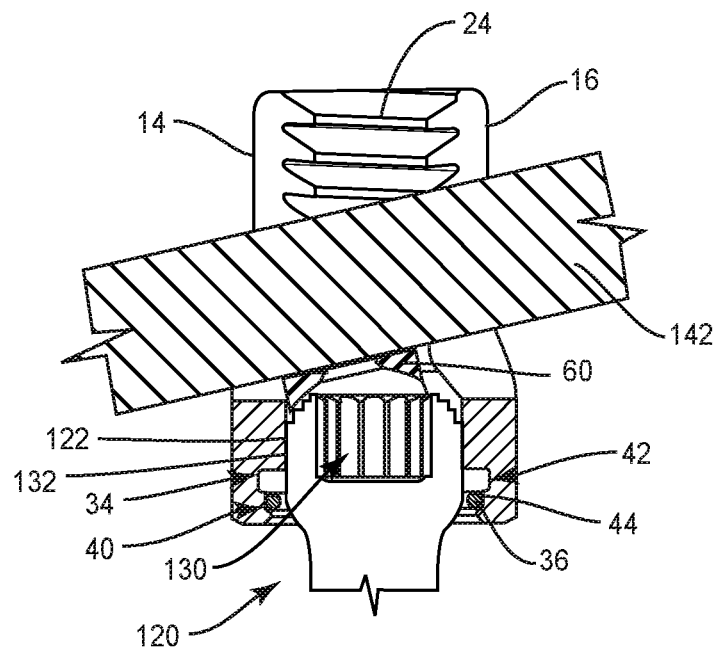
FIG. 6 is a break away, side, cross sectional view of components of the spinal implant system shown in FIG. 1.

Wall 22 defines a cavity, such as, for example, a groove 34 configured for disposal of an element, such as, for example, a snap ring 36, as shown in FIGS. 5 and 6, for example. Ring 36 includes a circumference that extends between ends defining an opening, such as, for example, a gap 38 (FIG. 4), which facilitates expansion and contraction. Groove 34 includes a portion, such as for, example, a circumferential channel 40 having a diameter d1 and a portion, such as, for example, a circumferential channel 42 having a diameter d2, as shown in FIG. 5. In some embodiments, diameter d2 is greater than diameter d1.

Channel 42 is disposed adjacent and proximal to channel 40. Channel 42 is separated from channel 40 by a protrusion, such as, for example, a lip 44. In some embodiments, bone anchor 120 is manually engageable with receiver 14 and/or bone anchor 120 is coupled with receiver 14 in a non-instrumented assembly such that ring 36 translates from and into channels 40, 42, and over lip 44. In some embodiments, ring 36 is expandable and resilient between a contracted and/or capture orientation, as shown for example in FIGS. 5-7 and an expanded orientation (not shown) for assembly of bone anchor 120 with receiver 14.

Wall 22 includes a cavity, such as, for example, a slot 54 configured to receive a flange of a part, such as, for example, a crown 60, as shown in FIG. 5, for example. Wall 22 includes an inner profile that defines a perimeter of cavity 20. Crown 60 is configured for disposal within the inner profile of wall 22 and/or the perimeter of cavity 20 of receiver 14. Crown 60 includes an outer profile and/or perimeter that fits within the inner profile of wall 22. An outer surface of crown 60 engages wall 22. In some embodiments, crown 60 is rotatable about axis X1 and configured to rotate relative to wall 22. In some embodiments, crown 60 is translatable within slot 54 such that crown 60 is translatable relative to wall 22 and along axis X1. In some embodiments, this configuration facilitates translation of crown 60 within slot 54, which facilitates positioning of a head 122 with receiver 14 so that head 122 can be locked with receiver 14, as described herein.

Figure 3A:
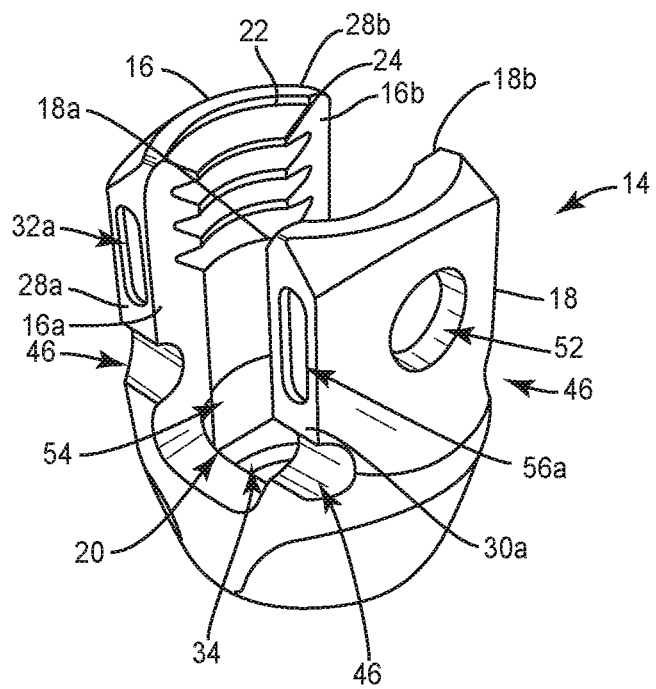
FIG. 3A is a perspective view of a component of the spinal implant system shown in FIG. 1.
Figure 3B:
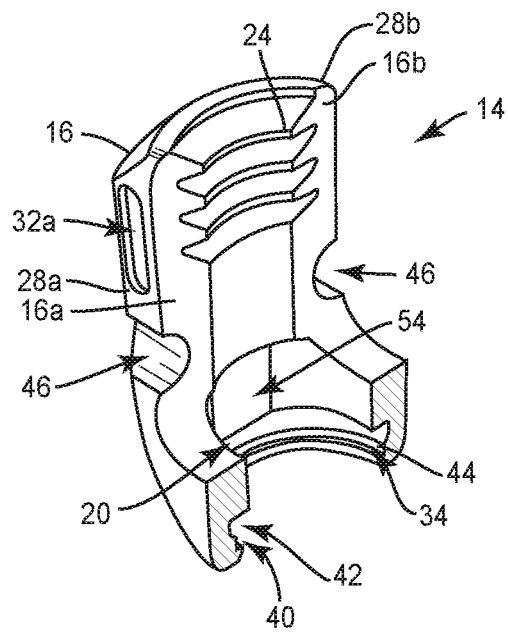
FIG. 3B is a perspective, cross sectional view of a component of the spinal implant system shown in FIG. 1.
Figure 3C:
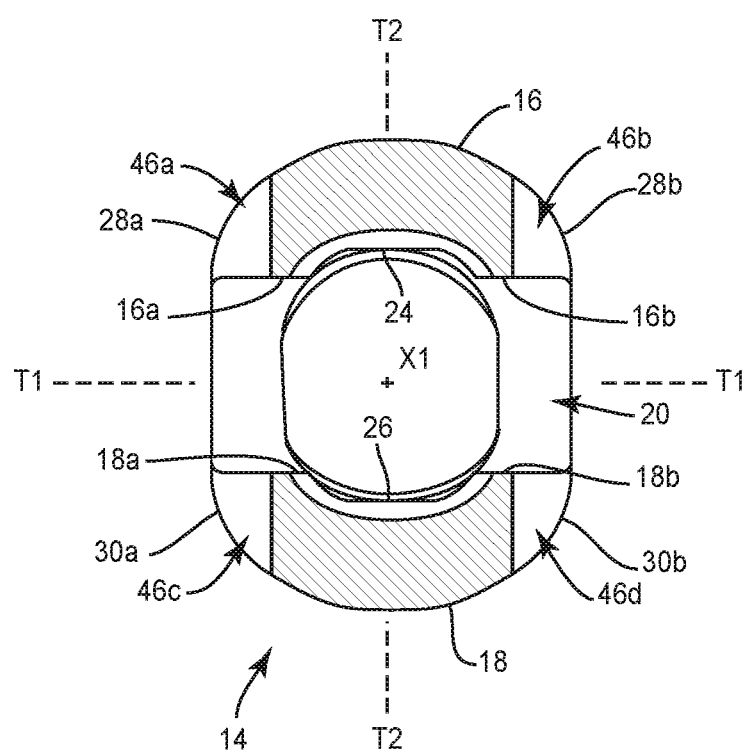
FIG. 3C is a perspective, cross sectional view of a component of the spinal implant system shown in FIG. 1.

Arm 16 extends between a first end that includes an end surface 16a and an opposite second end that includes end surface 16b. Arm 16 has an outer surface opposite thread form 24 that extends between end surfaces 16a, 16b. In some embodiments, end surface 16a and end surface 16b each extend parallel to longitudinal axis X1. In some embodiments, end surface 16a and end surface 16b extend parallel to one another along a first transverse axis T1 (FIG. 3C) defined by cavity 20 of receiver 14. In some embodiments, the outer surface of arm 16 includes a recess 50 (FIG. 7) configured for disposal of instrumentation, as discussed herein. In some embodiments, recess 50 is a blind hole that extends into the outer surface of arm 16 without extending through the inner surface of arm 16. That is, recess 50 is not in communication with cavity 20. In some embodiments, arm 16 includes a vertical surface 28a at the first end of arm 16 and a vertical surface 28b at the second end of arm 16. In some embodiments, vertical surface 28a and vertical surface 28b each extend parallel to longitudinal axis X1. In some embodiments, vertical surfaces 28a, 28b each extend transverse to end surfaces 16a, 16b. In some embodiments, vertical surface 28a and vertical surface 28b each extend parallel to one another along a second transverse axis T2 (FIG. 3C). In some embodiments, vertical surface 28a includes a vertical slot 32a and vertical surface 28b includes a vertical slot 32b. Vertical slots 32a, 32b are configured for disposal of instrumentation, as discussed herein.

In some embodiments, recess 50, vertical slot 32a and/or vertical slot 32b can have various shape configurations, such as, for example, circular, oval, oblong, polygonal, irregular, uniform, non-uniform, variable and/or tapered. In some embodiments, end surface 16a may be disposed at alternate orientations, relative to end surface 16b, such as, for example, parallel, transverse, perpendicular and/or other angular orientations such as acute or obtuse, co-axial and/or may be offset or staggered. In some embodiments, vertical surface 28a may be disposed at alternate orientations, relative to vertical surface 28b, such as, for example, parallel, transverse, perpendicular and/or other angular orientations such as acute or obtuse, co-axial and/or may be offset or staggered. In some embodiments, vertical surfaces 28a, 28b may be disposed at alternate orientations, relative to end surfaces 16a, 16b, such as, for example, parallel, transverse, perpendicular and/or other angular orientations such as acute or obtuse, co-axial and/or may be offset or staggered.

Arm 18 extends between a first end that includes an end surface 18a and an opposite second end that includes end surface 18b. Arm 18 has an outer surface that extends between end surfaces 18a, 18b. In some embodiments, end surface 18a and end surface 18b extend parallel to longitudinal axis X1. In some embodiments, end surfaces 16a, 16b extend parallel to end surfaces 18a, 18b. In some embodiments, end surface 18a and end surface 18b extend parallel to one another along first transverse axis T1 (FIG. 3C). In some embodiments, the outer surface of arm 18 includes a recess 52 (FIG. 7) configured for disposal of instrumentation, as discussed herein. In some embodiments, recess 52 is a blind hole that extends into the outer surface of arm 16 without extending through the inner surface of arm 16. That is, recess 52 is not in communication with cavity 20. In some embodiments, arm 18 includes a vertical surface 30a at the first end of arm 18 and a vertical surface 30b at the second end of arm 18. In some embodiments, vertical surface 30a and vertical surface 30b each extend parallel to longitudinal axis X1. In some embodiments, vertical surfaces 30a, 30b extends parallel to vertical surfaces 28a, 28b. In some embodiments, vertical surfaces 30a, 30b each extend transverse to end surfaces 18a, 18b. In some embodiments, vertical surface 30a and vertical surface 30b each extend parallel to one another along second transverse axis T2 (FIG. 3C). In some embodiments, vertical surface 30a includes a vertical slot 56a and vertical surface 30b includes a vertical slot 56b. Vertical slots 56a, 56b are configured for disposal of instrumentation, as discussed herein.

In some embodiments, recess 52, vertical slot 56a and/or vertical slot 56b can have various shape configurations, such as, for example, circular, oval, oblong, polygonal, irregular, uniform, non-uniform, variable and/or tapered. In some embodiments, end surface 18a may be disposed at alternate orientations, relative to end surface 18b, such as, for example, parallel, transverse, perpendicular and/or other angular orientations such as acute or obtuse, co-axial and/or may be offset or staggered. In some embodiments, vertical surface 30a may be disposed at alternate orientations, relative to vertical surface 30b, such as, for example, parallel, transverse, perpendicular and/or other angular orientations such as acute or obtuse, co-axial and/or may be offset or staggered. In some embodiments, vertical surfaces 30a, 30b may be disposed at alternate orientations, relative to end surfaces 18a, 18b, such as, for example, parallel, transverse, perpendicular and/or other angular orientations such as acute or obtuse, co-axial and/or may be offset or staggered.

Receiver 14 includes at least one mating element, such as, for example, at least one lateral groove 46 that extends into or through arm 16 and/or arm 18. Groove 46 is configured for disposal of a tool or instrument, such as, for example, a parallel distractor 48 (FIG. 1). Distractor 48 is configured to rotate receiver 14 relative to bone anchor 120. In some embodiments, groove 46 extends through each of arms 16, 18 such that a tip 58 of distractor 48 can extend into either arm 16 or arm 18, depending upon the manner in which a medical practitioner wishes to move receiver 14 relative to bone anchor 120, for example. In some embodiments, groove 46 extends into or through one of arms 16, 18 without extending into or through the other one of arms 16, 18. In some embodiments, groove 46 extends transverse to longitudinal axis X1. In some embodiments, groove 46 has a non-linear and/or arcuate configuration, such as, for example a concave configuration. In some embodiments, groove 46 has a continuous radius of curvature. In some embodiments, groove 46 is configured to form a snap fit connection with tip 58 of distractor 48 to provisionally lock tip 58 with groove 46. In some embodiments, groove 46 is configured to form a friction fit with tip 58 of distractor 48 to provisionally lock tip 58 with groove 46. In some embodiments, groove 46 is free of any flat or planar portions. In some embodiments, groove 46 is V-shaped. In some embodiments, groove 46 may be disposed at alternate orientations, relative to longitudinal axis X1, such as, for example, parallel, transverse, perpendicular and/or other angular orientations such as acute or obtuse, co-axial and/or may be offset or staggered. In some embodiments, all or only a portion of groove 46 may be variously configured and dimensioned, such as, for example, concave, polygonal, irregular, uniform, non-uniform, staggered, tapered, consistent or variable.

Figure 2A:
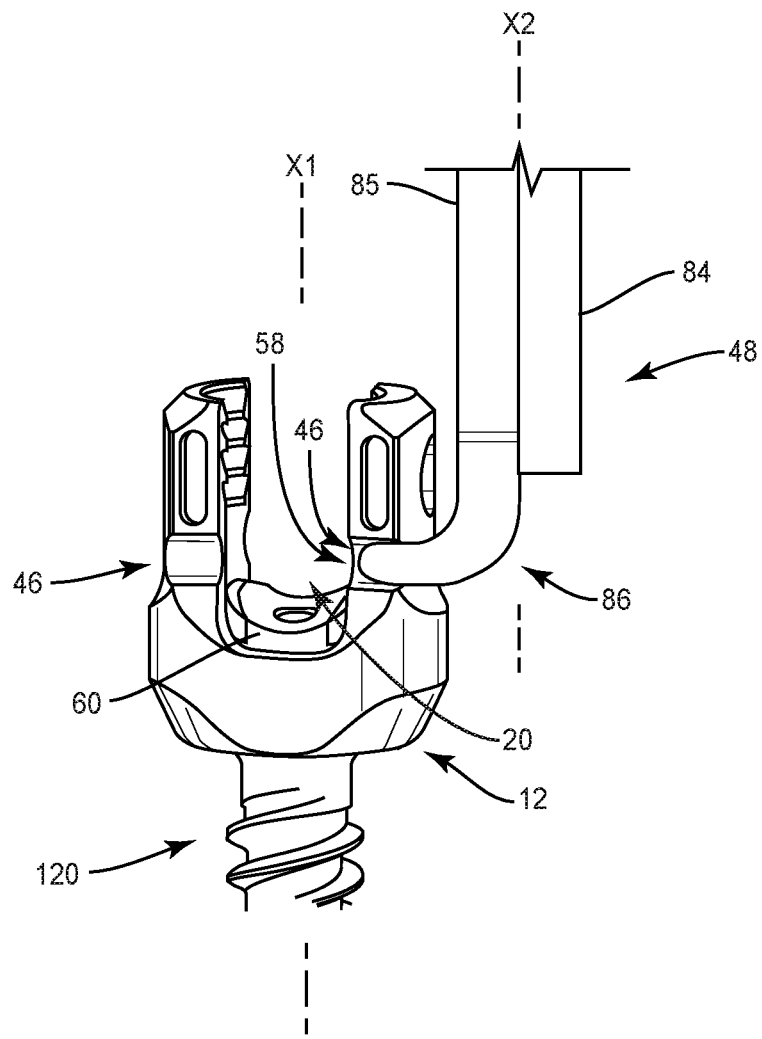
FIG. 2A is a break away, side view of components of the spinal implant system shown in FIG. 1.

In some embodiments, distractor 48 comprises a shaft 84 that extends along a longitudinal axis X2, as shown in FIG. 2A. Shaft 84 has a length along longitudinal axis X2 such that at least a portion of shaft 84 is configured to extend out of a patient when tip of distractor 48 engages groove 46 and bone anchor 120 is implanted within tissue of the patient. Distractor 48 includes a mating element, such as, for example, a hook 86 that extends from shaft 84. Hook 86 is fixed relative to shaft 84 such that moving shaft 84 will also move hook 86, and vice versa. A distal end of hook 86 includes tip 58. Hook 86 extends transverse to longitudinal axis X2. In some embodiments, hook 86 is tapered from shaft 84 to tip 58. In some embodiments, hook 86 is continuously tapered from shaft 84 to tip 58. In some embodiments, hook 86 has an arcuate configuration. In some embodiments, hook 86 has a cylindrical configuration. In some embodiments, shaft 84 extends parallel to receiver 14 and/or longitudinal axis X1 when hook 86 is positioned within groove 46. In some embodiments, bone anchor 120 is offset from longitudinal axis X2 when hook 86 is positioned within groove 46. In some embodiments, distractor 48 includes a handle 85 that extends from shaft 84. In some embodiments, handle 85 includes gripping features, such as, for example, indentations and/or protrusions configured to facilitate gripping. In some embodiments, hook 86 may have various cross section configurations, such as, for example, circular, oval, oblong, triangular, rectangular, square, polygonal, irregular, uniform, non-uniform, variable, tubular and/or tapered. In some embodiments, hook 86 may be disposed at alternate orientations, relative to longitudinal axis X2, such as, for example, transverse, perpendicular and/or other angular orientations such as acute or obtuse, co-axial and/or may be offset or staggered. In some embodiments, handle 85 may have various surface configurations to enhance gripping, such as, for example, rough, arcuate, undulating, porous, semi-porous, dimpled, polished and/or textured.

In some embodiments, groove 46 includes a groove 46a that extends into the first end of arm 16, and/or a groove 46b that extends into the second end of arm 16, and/or a groove 46c that extends into the first end of arm 18, and/or a groove 46d that extends into the second end of arm 18, as shown in FIG. 3C. Groove 46a extends through the outer surface of arm 16, through vertical surface 28a of arm 16 and through end surface 16a of arm 16. Groove 46b extends through the outer surface of arm 16, through vertical surface 28b of arm 16 and through end surface 16b of arm 16. Groove 46c extends through the outer surface of arm 18, through vertical surface 30a of arm 18 and through end surface 18a of arm 18. Groove 46d extends through the outer surface of arm 18, through vertical surface 30b of arm 18 and through end surface 18b of arm 18. Groove 46a is coaxial with groove 46c. Groove 46b is coaxial with groove 46d. Grooves 46a-d provide a medical practitioner options as to where to engage distractor 48 with receiver 14. For example, one of grooves 46a-d may be preferable over another of grooves 46a-d when it is desired to move receiver 14 relative to bone anchor 120 in a given direction to achieve a desired orientation. Providing grooves 46a-d such that grooves 46a-d extend through the outer surfaces of arms 16, 18, through the vertical surfaces of arms 16, 18, and through the end surfaces of arms 16, 18 allows tip 58 of distractor 48 to extend completely through a respective one of grooves 46a-d. In some embodiments, tip 58 of distractor 48 is configured to extend completely through a respective one of grooves 46a-d and into cavity 20 of receiver 14 to maximize engagement between distractor 48 and receiver 14 to ensure a secure connection between distractor 48 and receiver 14 that will allow distractor 48 to rotate receiver 14 relative to bone anchor 120. In some embodiments, tip 58 of distractor 48 is configured to extend completely through a respective one of grooves 46a-d and into cavity 20 of receiver 14 such that tip 58 will contact rod 142 when rod 142 is positioned in cavity 20 to provide the medical practitioner tactile feedback that tip 58 is properly engaged with receiver 14.

Figure 3D:
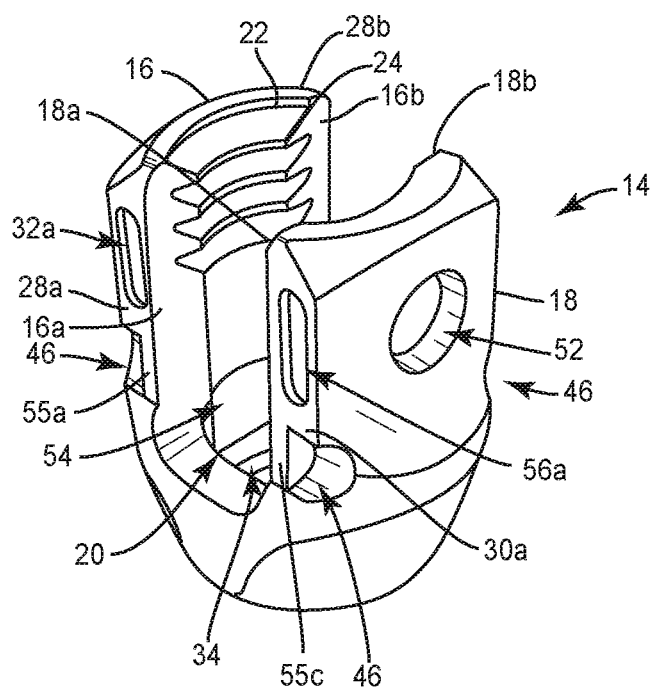
FIG. 3D is a perspective view of one embodiment of a component of the spinal implant system shown in FIG. 1 in accordance with the principles of the present disclosure.
Figure 3E:
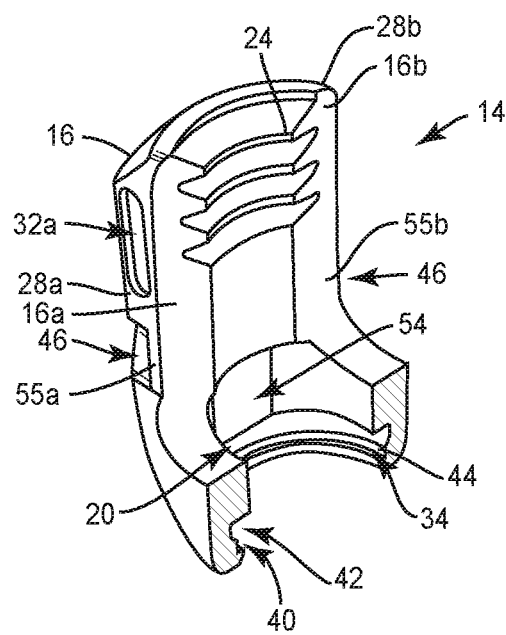
FIG. 3E is a perspective, cross sectional view of the component shown in FIG. 3D.
Figure 3F:
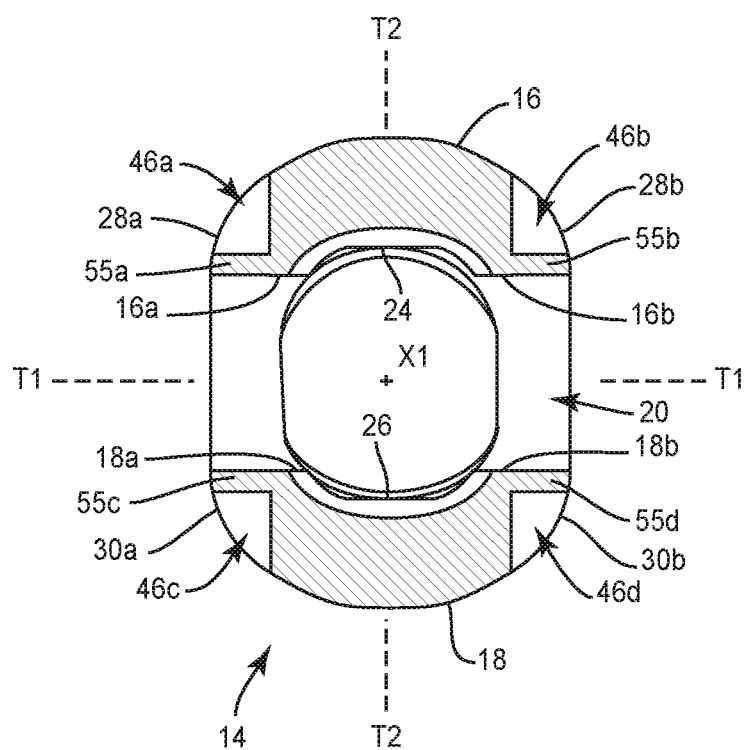
FIG. 3F is a perspective, cross sectional view of the component shown in FIG. 3D.

In some embodiments, receiver 14 includes a wall 55a positioned between the outer surface of arm 16 and end surface 16a of arm 16 such that groove 46a extends through the outer surface of arm 16 and through vertical surface 28a of arm 16 without extending through end surface 16a of arm 16, as shown in FIGS. 3D-F. In some embodiments, receiver 14 includes a wall 55b positioned between the outer surface of arm 16 and end surface 16b of arm 16 such that groove 46b extends through the outer surface of arm 16 and through vertical surface 28b of arm 16 without extending through end surface 16b of arm 16, as shown in FIGS. 3D-F. In some embodiments, receiver 14 includes a wall 55c positioned between the outer surface of arm 18 and end surface 18a of arm 18 such that groove 46c extends through the outer surface of arm 18 and through vertical surface 30a of arm 18 without extending through end surface 18a of arm 18, as shown in FIGS. 3D-F. In some embodiments, receiver 14 includes a wall 55d positioned between the outer surface of arm 18 and end surface 18b of arm 18 such that groove 46d extends through the outer surface of arm 18 and through vertical surface 30b of arm 18 without extending through end surface 18b of arm 18, as shown in FIGS. 3D-F. The configuration described above and shown in FIGS. 3D-F allows an end surface of tip 58 of distractor 48 to engage one of walls 55a-d when tip 58 is inserted in to one of grooves 46a-d. It is envisioned that this may provide a medical practitioner with tactile feedback that tip 58 of distractor 48 is fully inserted into one of grooves 46a-d.

Distractor 48 is engageable with groove 46 to rotate receiver 14 relative to bone anchor 120 about a rotation axis R1 that extends transverse to longitudinal axis X1. As shown in FIGS. 1 and 2, rotation axis R1 lies in the same plane as rod 142 when rod 142 is positioned within cavity 20 of receiver 14. This configuration allows for lateral rotation of receiver 14 at the center of rotation of rod 142, rather than at the head of bone anchor 120.

Figure 4:
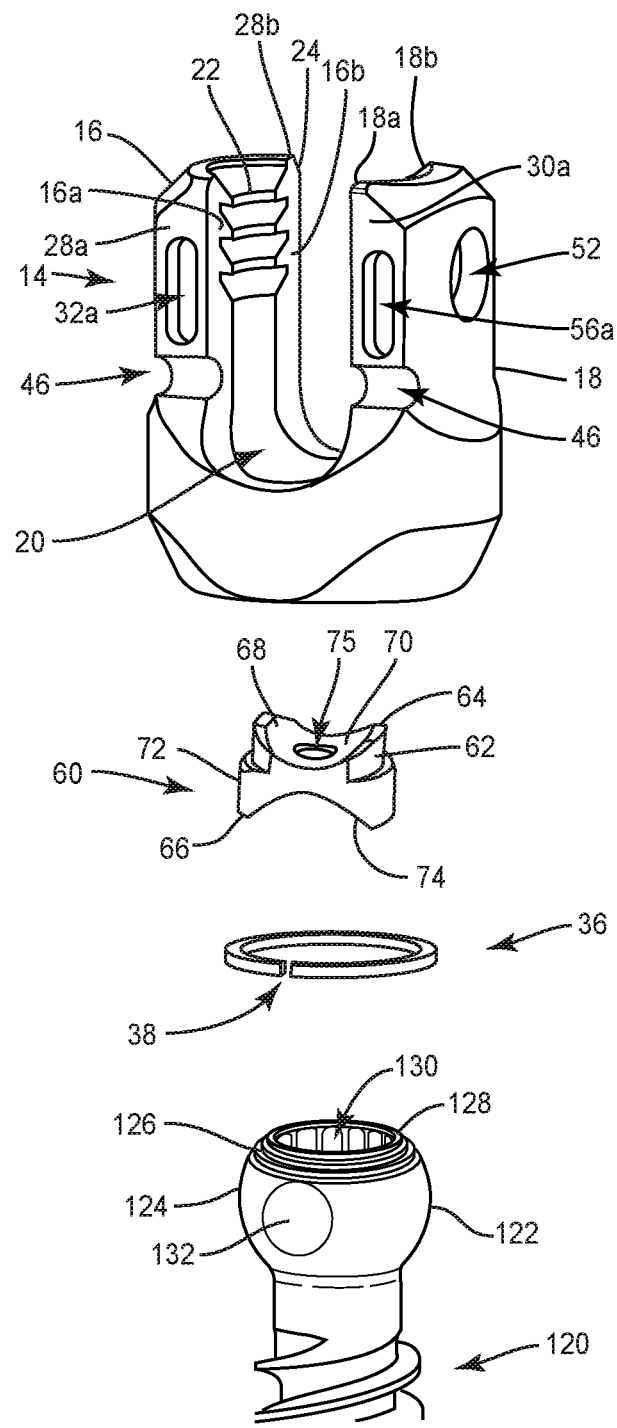
FIG. 4 is a break away, perspective view of components of the spinal implant system shown in FIG. 1 with parts separated.

Crown 60 is configured for disposal within cavity 20 of receiver 14. Crown 60 includes a wall 62 having an end surface 64 and an end surface 66, as shown in FIG. 4. Surface 64 is configured to define at least a portion 68 of cavity 20. Portion 68 is defined by an outer surface 70 that defines a curved portion of crown 60 configured for engagement with rod 142. In some embodiments, crown 60 includes an aperture 75 that extends continuously through end surfaces 64, 66. In some embodiments, aperture 75 is configured for disposal of a guidewire or K-wire to allow components of system 10 to be delivered to a surgical site along the guidewire. In some embodiments, all or only a portion of surface 70 may have alternate cross section configurations, such as, for example, oval, oblong, triangular, square, polygonal, irregular, uniform, non-uniform, offset, staggered, and/or tapered. In some embodiments, crown 60 does not include aperture 75. Rather, end surfaces 64, 66 are free of any openings.

Crown 60 includes a flange 72 configured for mating engagement with the surfaces that define slot 54 and wall 22. In some embodiments, engagement of flange 72 and the surfaces that define slot 54 and wall 22 resist and/or prevent axial translation of crown 60 relative to wall 22 of receiver 14. Surface 70 is disposed in alignment with wall 22 for disposal of rod 142. Surface 66 defines an engagement portion 74 configured for engagement with bone anchor 120, as described herein.

Bone anchor 120 is configured to penetrate tissue, such as, for example, bone. Bone anchor 120 comprises a head 122 having a substantially spherical proximal portion configured for moveable disposal with receiver 14 and crown 60. Head 122 includes a surface 124 that defines a plurality of ridges 126 to improve purchase of head 122 with crown 60. Head 122 includes a surface 128 that is substantially flat. Engagement portion 74 of crown 60 is configured to engage surface 128 and/or ridges 126 of head 122 to fix receiver 14 relative to bone anchor 120, as discussed herein.

In some embodiments, bone anchor 120 includes a socket 130 that extends into surface 128. Socket 130 has a hexalobe geometry configured for disposal of a similarly shaped bit of a tool, such as, for example, a driver (not shown) to engage the driver with head 122 to rotate bone anchor 120. In some embodiments, socket 130 has a maximum width that is greater than that of aperture 75 of crown such that a driver configured to mate with socket 130 would be too large to pass through aperture 75. In such embodiments, it may be required that bone anchor 120 be implanted prior to engaging receiver 14 with bone anchor 120. In some embodiments, it may be required that bone anchor 120 be rotated relative to a patient's anatomy such that bone anchor penetrates tissue by coupling an instrument to a portion of bone anchor other than socket 130.

In some embodiments, socket 130 has a maximum width that is less than or equal to that of aperture 75 of crown such that a driver configured to mate with socket 130 can be positioned through aperture 75 and into socket 130. Socket 130 is in communication with cavity 20 such that the driver may be inserted between arms 16, 18 and translated axially through aperture 75 of crown 60, until the bit of the driver is disposed in socket 130. In some embodiments, socket 130 has a cruciform, phillips, square, hexagonal, polygonal, star cross sectional configuration configured for disposal of a correspondingly shaped portion of a driver.

In some embodiments, head 122 of bone anchor 120 includes a pair of flats 132 that are positioned opposite one another such that flats 132 extend parallel to one another along a horizontal axis that extends perpendicular to longitudinal axis X1. In some embodiments, flats 132 each extend parallel to longitudinal axis X1. Flats 132 are each configured to engage planar surfaces 80 of receiver 14 (FIG. 6) such that bone anchor 120 is rotatable relative to receiver 14 in only one plane, such as, for example, a sagittal plane, a transverse plane, or a coronal plane of a patient. It is envisioned that the plane in which bone anchor 120 is rotatable relative to receiver 14 in may be selected by the manner in which bone anchor 120 is inserted into the anatomy of the patient. For example, if it is desired that bone anchor 120 be rotatable relative to receiver 14 in the sagittal plane of the patient, bone anchor 120 may be inserted into the patient such that flats 132 are each parallel with the sagittal plane; if it is desired that bone anchor 120 be rotatable relative to receiver 14 in the coronal plane of the patient, bone anchor 120 may be inserted into the patient such that flats 132 are each parallel with the coronal plane; and if it is desired that bone anchor 120 be rotatable relative to receiver 14 in the transverse plane of the patient, bone anchor 120 may be inserted into the patient such that flats 132 are each parallel with the transverse plane.

In assembly, operation and use, spinal implant system 10, similar to the systems and methods described herein, includes bone screw 12 described herein, a coupling member, such as, for example, set screw 140 and an implant, such as, for example, spinal rod 142. The components of spinal implant system 10 are employed with a surgical procedure for treatment of a spinal disorder affecting a section of a spine (not shown) of a patient, as discussed herein. Spinal implant system 10 is employed with a surgical procedure for treatment of a condition or injury of an affected section of the spine. One or more bone screws 12 and one or a plurality of spinal implants, such as, for example, vertebral rods can be delivered or implanted as a pre-assembled device or can be assembled in situ. The components of spinal implant system 10 may be may be completely or partially revised, removed or replaced.

In some embodiments, bone anchor 120 is threaded and engaged with tissue, such as, for example, vertebrae. In some embodiments, bone screw 12 is disposed adjacent vertebrae at a surgical site. A bit of a driver is inserted through aperture 75 of crown and into socket 130. The driver is rotated or otherwise manipulated to drive, torque, insert or otherwise connect bone screw 12 with vertebrae. A receiver 14 is selected for assembly with bone anchor 120 such that one or more bone screws 12 have a selected movement of its component parts and/or movement relative to tissue. In some embodiments, receiver 14 is engaged with head 122 after bone anchor 120 is engaged with tissue by causing ring 36 to translate, expand and engage groove 34 of receiver 14 such that head 122 translates through ring 36 and is assembled with receiver 14. In some embodiments, head 122 may be assembled with receiver 14 and ring 36 may be assembled with groove 34. In some embodiments, receiver 14 is attached with bone anchor 120 such that receiver 14 is selectively and rotatable relative to bone anchor 120 within a transverse plane of vertebrae.

In some embodiments, a tip of a guidewire is positioned within tissue, adjacent a surgical site. Bone anchor 120, crown 60, snap ring 36 and bone anchor 120 are threaded along the guidewire. Bone anchor 120, crown 60, snap ring 36 and bone anchor 120 are translated along the guidewire to the surgical site. An instrument is used to engage flats 132 and rotate bone anchor 120 relative to the patient's anatomy such that bone anchor 120 penetrates tissue. Receiver 14 is engaged with bone anchor 120 by causing ring 36 to translate, expand and engage groove 34 of receiver 14 such that head 122 translates through ring 36 and is assembled with receiver 14.

Figure 10:
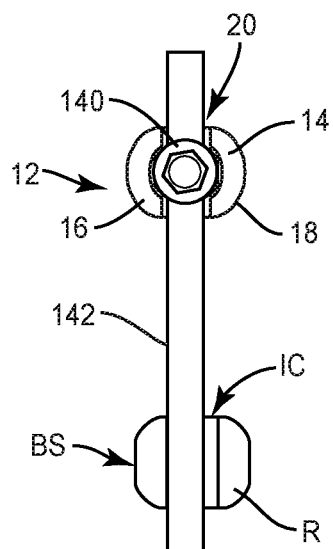
FIG. 10 is a plan view of components of the spinal implant system shown in FIG. 1.

One end of rod 142 is positioned within cavity 20 of receiver 14 and an opposite end of rod 142 is positioned adjacent a bone screw BS, as shown in FIG. 10. However, the opposite end of rod 142 is not aligned with an implant cavity IC of bone screw BS defined by a receiver R of bone screw BS such that the opposite end of rod 142 is not capable of being disposed within implant cavity IC of bone screw BS, as shown in FIG. 10. In some embodiments, bone screw BS is a bone screw similar to bone fastener 12. In some embodiments, threads on an outer surface of set screw 140 are aligned with threads 24, 26 and set screw 140 is rotated relative to receiver 14 such that set screw 140 is translated into engagement with spinal rod 142. Spinal rod 142 applies a force to crown 60 and crown 60 applies a force upon head 122 of bone anchor 120. However, set screw 140 is not fully threaded into receiver 14 such that receiver 14 is able to rotate relative to bone anchor 120.

Figure 11:
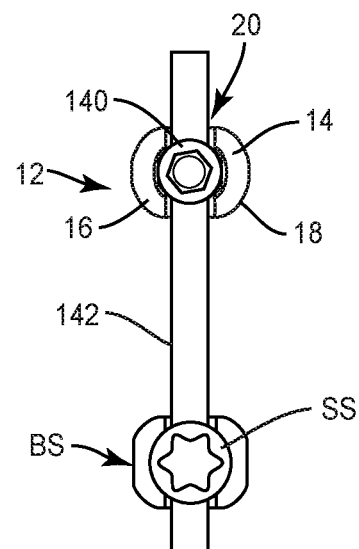
FIG. 11 is a plan view of components of the spinal implant system shown in FIG. 1.

Distractor 48 engages bone fastener 12 by positioning tip 58 of distractor 48 within groove 46 (e.g., any one of grooves 46a-d). Distractor 48 is then manipulated to move receiver 14 relative to bone anchor 120. As distractor 48 moves receiver 14 relative to bone anchor 120, the opposite end of rod 142 moves relative to bone screw BS such that the opposite end of rod 142 is aligned with implant cavity IC of bone screw BS such that the opposite end of rod 142 is disposed within implant cavity IC of bone screw BS, as shown in FIG. 11.

Figures 7, 8, 9:
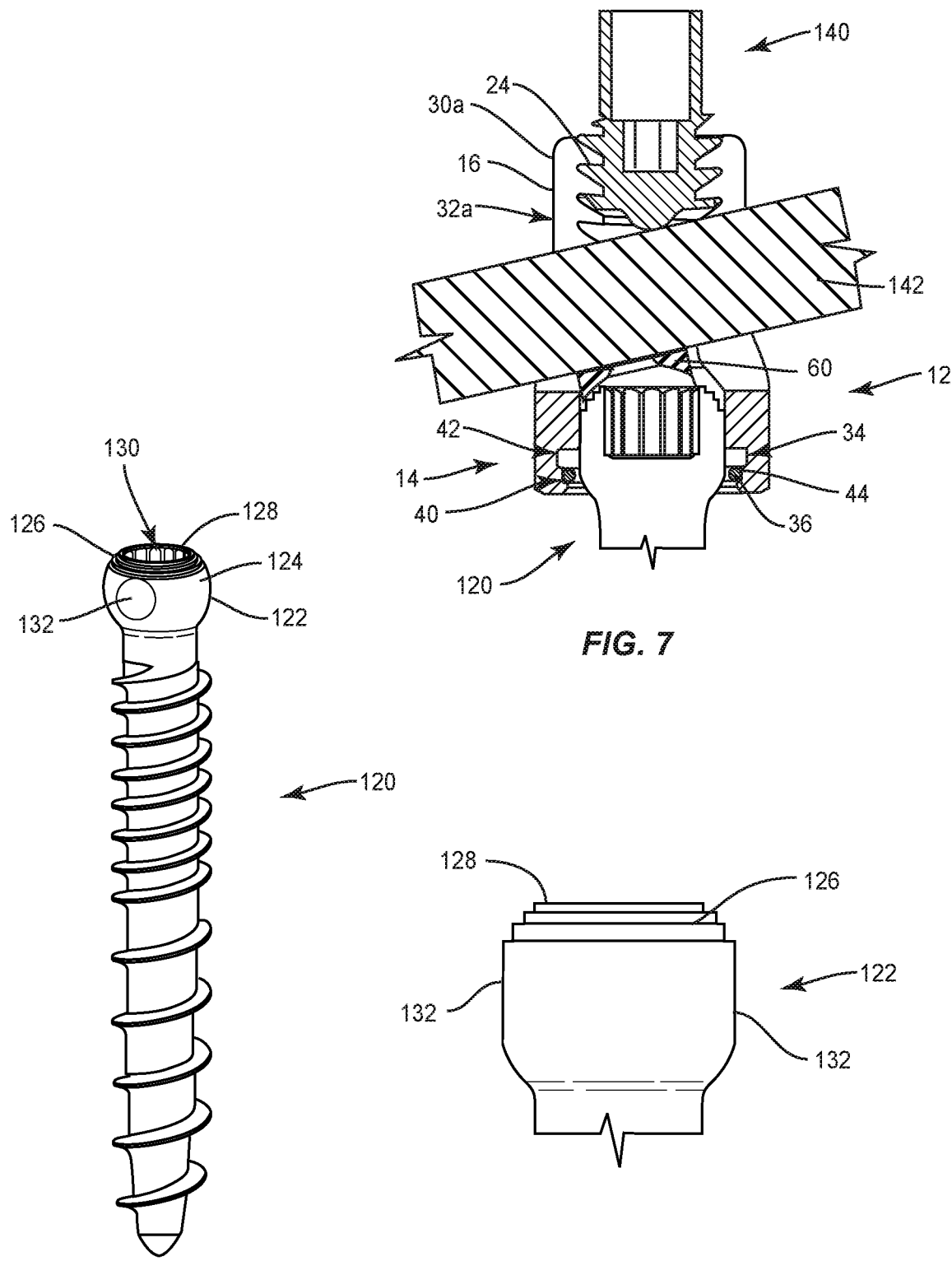
FIG. 7 is a break away, side, cross sectional view of components of the spinal implant system shown in FIG. 1.
FIG. 8 is a perspective view of a component of the spinal implant system shown in FIG. 1.
FIG. 9 is a break away, side, detailed view of a component of the spinal implant system shown in FIG. 1.

Set screw 140 may be fully threaded with receiver such that crown 60 applies a force upon head 122 of bone anchor 120 sufficient to fix receiver 14 relative to bone anchor. In some embodiments, set screw 140 has a tapered tip that engages rod 142, as shown in FIG. 7. This configuration allows set screw 140 to engage rod 142 and fix receiver 14 relative to bone anchor 120, regardless of the orientation of rod 142 relative to receiver 14 or bone anchor 120. In some embodiments, a second set screw SS is threaded with receiver R of bone screw BS such that set screw SS engages rod 142 to fix rod 142 relative to bone screw BS.

Figure 12:
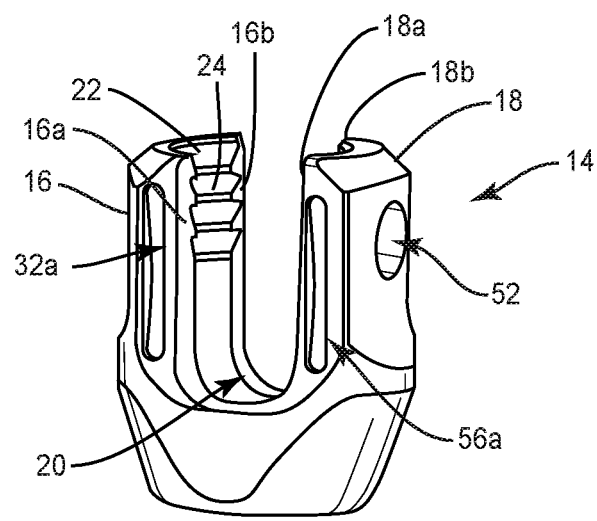
FIG. 12 is a perspective view of one embodiment of a component of the spinal implant system shown in FIG. 1.

In one embodiment, shown in FIG. 12, receiver 14 does not include groove 46. Rather, the lengths of vertical slots 32a, 32b of arm 16 and vertical slots 56a, 56b of arm 18 are extended. Vertical slots 32a, 32b, 56a, 56b each include a top portion and a bottom portion and an intermediate portion between the top and bottom portions. In some embodiments, vertical slots 32a, 32b, 56a, 56b each have a depth that is greater at the intermediate portion than at the top portion or the bottom portion. That is, the depth of each of vertical slots 32a, 32b, 56a, 56b increases from the top portion to the intermediate portion and from the bottom portion to the intermediate portion. The instrumentation discussed above may be inserted into the top portions or the bottom portions of at least one of vertical slots 32a, 32b, 56a, 56b to move receiver 14 relative to bone anchor 120 in the manner discussed above and tip 58 of distractor 48 may be inserted into the intermediate portions of one of vertical slots 32a, 32b, 56a, 56b to move receiver 14 relative to bone anchor 120 in the manner discussed above. In some embodiments, the intermediate portion of each of vertical slots 32a, 32b, 56a, 56b is positioned in the same plane as groove 46 in the embodiment shown in FIGS. 1-11 to allow receiver 14 to rotate relative to bone anchor 120 at rod 142. In some embodiments, distractor 48 is engageable with the intermediate portion of each of vertical slots 32a, 32b, 56a, 56b to rotate receiver 14 relative to bone anchor 120 about a rotation axis that is positioned and oriented in the same manner as rotation axis R1.

Figure 13:
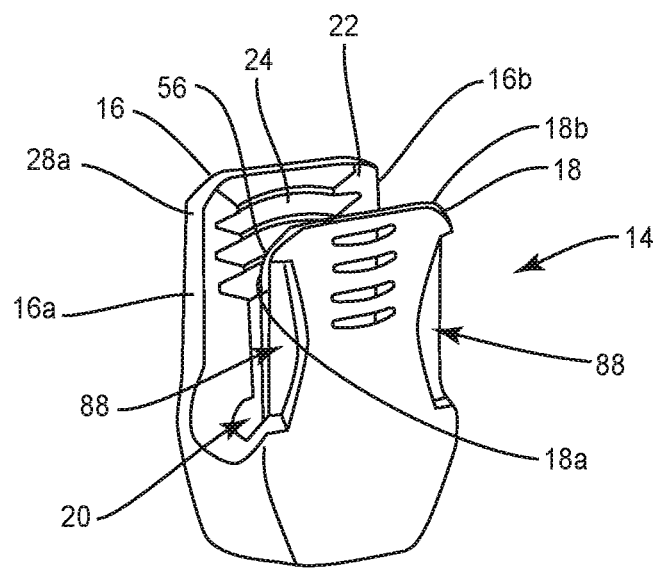
FIG. 13 is a perspective view of one embodiment of a component of the spinal implant system shown in FIG. 1.

In one embodiment, shown in FIG. 13, receiver 14 does not include groove 46. Rather, receiver 14 includes a pair of slots 88 in arm 16 and a pair of slots 88 in arm 18. One of slots 88 in arm 16 extends into the outer surface of arm 16 and vertical surface 28a and the other slot 88 in arm 16 extends into the outer surface of arm 16 and vertical surface 28b. One of slots 88 in arm 18 extends into the outer surface of arm 18 and vertical surface 30a and the other slot 88 in arm 18 extends into the outer surface of arm 18 and vertical surface 30b. Slots 88 each have a top portion, a bottom portion and an intermediate portion positioned between the top and bottom portions. The intermediate portions each have a width that is greater than that of the top portions or the bottom portions. That is, the width of each of grooves 88 increases from the top portion to the intermediate portion and from the bottom portion to the intermediate portion. The instrumentation discussed above may be inserted into the top portions or the bottom portions of at least one of grooves 88 to move receiver 14 relative to bone anchor 120 in the manner discussed above and tip 58 of distractor 48 may be inserted into the intermediate portions of one of grooves 88 to move receiver 14 relative to bone anchor 120 in the manner discussed above. In some embodiments, the intermediate portion of each of grooves 88 is positioned in the same plane as groove 46 in the embodiment shown in FIGS. 1-11 to allow receiver 14 to rotate relative to bone anchor 120 at rod 142. In some embodiments, distractor 48 is engageable with the intermediate portion of each of grooves 88 to rotate receiver 14 relative to bone anchor 120 about a rotation axis that is positioned and oriented in the same manner as rotation axis R1.

In some embodiments, spinal implant system 10 comprises a spinal implant kit, which includes a plurality of members, such as, for example, implant receivers 14. In some embodiments, the implant receivers may include any of the implant receivers 14 shown in FIGS. 1-11 and/or described above. Receivers 14 are connectable with an interchangeable member, such as, for example, bone anchor 120. In some embodiments, receiver 14 is configured for selection from the implant receivers 14 such that receiver 14 is connectable with a compatible bone anchor 120.

In some embodiments, an interchangeable mating element, such as, for example, a head 122 of bone anchor 120 is interchangeable with a mating element, as described herein, of each of the implant receivers 14 to form a selected bone screw 12 having a selected movement of its component parts and/or movement relative to tissue. In some embodiments, the selected movement includes rotation and/or pivotal movement of bone anchor 120 relative to receiver 14 about one or a plurality of axes. In some embodiments, the selected movement includes rotation and/or pivotal movement of bone anchor 120 relative to receiver 14 through one or a plurality of planes. In some embodiments, bone anchor 120 is connected to a selected receiver 14 to comprise a multi-axial fastener. In some embodiments, bone anchor 120 is connected to a selected receiver 14 to comprise a uni-axial fastener. In some embodiments, spinal implant system 10 comprises a spinal implant kit, which includes receivers 14 and alternate receivers, such as those described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments the agent may be a hydroxyapatite coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone screws 12 such as those described herein and/or fixation elements, which may be employed with a single vertebral level or a plurality of vertebral levels. In some embodiments, bone screws 12 may be engaged with vertebrae in various orientations, such as, for example, series, parallel, offset, staggered and/or alternate vertebral levels. In some embodiments, bone screws 12 may be configured as multi-axial screws, sagittal angulation screws, pedicle screws, mono-axial screws, uni-planar screws, fixed screws, anchors, tissue penetrating screws, conventional screws, and/or expanding screws. In some embodiments, bone screws 12 may be employed with wedges, anchors, buttons, clips, snaps, friction fittings, compressive fittings, expanding rivets, staples, nails, adhesives, posts, connectors, fixation plates and/or posts.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
an instrument comprising a shaft and a mating element extending from the shaft; and
a bone fastener comprising a bone anchor and a receiver having spaced apart first and second arms, the arms each including opposite inner and outer surfaces each extending from a first end surface to a second end surface, the receiver comprising a first groove extending into the first end surface of the first arm and a second groove extending into the first end surface of the second arm such that the second groove is coaxial with the first groove, the grooves each extending through the inner and outer surfaces of their respective arm, the mating element being configured for disposal in the grooves to move the receiver relative to the bone anchor, the first end surface of the first arm comprising a vertical slot positioned above the first groove such that the vertical groove is spaced apart from the inner and outer surfaces of the first arm.

2. The spinal implant system recited in claim 1, wherein the mating element is a hook that extends transverse to the shaft.

3. The spinal implant system recited in claim 1, wherein the inner surfaces each include a thread form.

4. The spinal implant system recited in claim 1, wherein the mating element is a hook that is tapered from the shaft to a tip of the hook.

5. The spinal implant system recited in claim 1, wherein the mating element is a hook having an arcuate configuration.

6. The spinal implant system recited in claim 1, wherein the mating element is a hook having a cylindrical configuration.

7. The spinal implant system recited in claim 1, wherein the inner surfaces each include a thread form and the outer surfaces each include a recess.

8. The spinal implant system recited in claim 1, wherein the mating element forms a snap fit with the grooves.

9. The spinal implant system recited in claim 1, wherein the mating element forms a friction fit with the grooves.

10. The spinal implant system recited in claim 1, wherein the shaft extends parallel to the receiver when the mating element engages the grooves.

11. The spinal implant system recited in claim 1, wherein the bone anchor is offset from a longitudinal axis defined by the shaft when the mating element engages the grooves.

12. The spinal implant system recited in claim 1, vertical groove comprises a top portion, a bottom portion and an intermediate portion between the top and bottom portions, the vertical slot having a depth that increases from the top portion to the intermediate portion and from the bottom portion to the intermediate portion.

13. The spinal implant system recited in claim 1, wherein the shaft has a length such that at least a portion of the shaft is configured to extend out of a patient when the mating element engages the grooves and the bone fastener is implanted within tissue of the patient.

14. The spinal implant system recited in claim 1, wherein the instrument is a parallel distractor.

15. The spinal implant system recited in claim 1, wherein the instrument is monolithic.

16. The spinal implant system recited in claim 1, wherein the hook is fixed relative to the shaft.

17. A spinal implant system comprising:
an instrument comprising a shaft and a hook extending from the shaft, the hook being fixed relative to the shaft, the hook extending transverse to the shaft; and
a bone fastener comprising a bone anchor and a receiver having spaced apart first and second arms, the arms each including opposite inner and outer surfaces each extending from a first end surface to an opposite second end surface, the inner surfaces defining an implant cavity, the bone fastener comprising a first groove extending into the first end surface of the first arm and a second groove extending into the first end surface of the second arm such that the second groove is coaxial with the first groove, the grooves each extending through the inner and outer surfaces of their respective arm, the hook being configured for disposal in the grooves to move the receiver relative to the bone anchor, the first end surface of the first arm comprising a vertical slot positioned above the first groove such that the vertical slot is spaced apart from the first groove and the inner and outer surfaces of the first arm.

18. The spinal implant system recited in claim 17, wherein the shaft extends parallel to the receiver when the hook is disposed in the grooves.

19. Spinal implant system recited in claim 17, wherein the bone anchor is offset from a longitudinal axis defined by the shaft when the hook is disposed in the grooves.

20. A spinal implant system comprising:
a bone fastener comprising a receiver having spaced apart first and second arms, the arms each including opposite inner and outer surfaces each extending from a first end surface to an opposite second end surface, the inner surfaces defining an implant cavity, the inner surfaces each including a thread form, the outer surfaces each including a recess, the bone fastener comprising a first groove extending into the first end surface of the first arm and a second groove extending into the first end surface of the second arm such that the second groove is coaxial with the first groove, the grooves each extending through the inner and outer surfaces of their respective arm, the first end surface of the first arm comprising a first vertical slot positioned above the first groove such that the first vertical slot is spaced apart from the first groove and the inner and outer surfaces of the first arm, the second end surface of the second arm comprising a second vertical slot positioned above the second groove such that the second vertical slot is spaced apart from the second groove and the inner and outer surfaces of the second arm, the bone fastener further comprising a bone anchor that is configured to penetrate tissue; and
an instrument comprising a shaft and a hook extending from the shaft, the hook being fixed relative to the shaft, the hook extending transverse to the shaft, the hook having an arcuate configuration, the hook being fixed to the shaft, the hook being tapered from the shaft to a tip of the hook, the hook being configured for disposal in the grooves to move the receiver relative to the bone anchor,
wherein the shaft extends parallel to the receiver when the hook is disposed in the grooves, and
wherein the bone anchor is offset from a longitudinal axis defined by the shaft when the hook is disposed in the grooves.

* * * * *